United States Patent [19]

Severini

[11] Patent Number: 5,779,729
[45] Date of Patent: Jul. 14, 1998

[54] COATED STENT

[75] Inventor: Aldo Severini, Milan, Italy

[73] Assignee: Istituto Nazionale Per Lo Studio E La Cura Dei Tumori, Milan, Italy

[21] Appl. No.: 597,379

[22] Filed: Feb. 8, 1996

Related U.S. Application Data

[63] Continuation of Ser. No. 253,740, Jun. 3, 1994, abandoned.

[30] Foreign Application Priority Data

Jun. 4, 1993 [IT] Italy ................... MI93A0176

[51] Int. Cl.⁶ ........................................ A61F 2/06
[52] U.S. Cl. ..................... 606/191; 623/1; 128/898
[58] Field of Search ....................... 606/191, 194, 606/195, 198; 623/1, 11, 12; 128/898

[56] References Cited

U.S. PATENT DOCUMENTS

| | | | |
|---|---|---|---|
| 4,512,338 | 4/1985 | Balko | 606/195 X |
| 4,728,328 | 3/1988 | Hughes et al. | 623/12 |
| 4,776,337 | 10/1988 | Palmaz | 623/1 |
| 4,922,905 | 5/1990 | Strecker | 606/195 |
| 5,019,090 | 5/1991 | Pinchuk | 606/108 X |
| 5,123,917 | 6/1992 | Lee | 623/1 |
| 5,133,742 | 7/1992 | Pinchuk | 623/1 |
| 5,197,978 | 3/1993 | Hess | 623/12 X |
| 5,234,457 | 8/1993 | Andersen | 606/108 X |
| 5,527,353 | 6/1996 | Schmitt | 623/12 |

*Primary Examiner*—Michael Peffley
*Attorney, Agent, or Firm*—Griffin, Butler, Whisenhunt & Szipl

[57] ABSTRACT

A coated stent, particularly a biocompatible polymeric material coated stent, and a coating process are herein described.

18 Claims, No Drawings

COATED STENT

This application is a continuation of Ser. No. 08/253,740, filed Jun. 3, 1994, now abandoned.

BACKGROUND OF THE INVENTION

The present invention relates to a coated stent, in particular to a biocompatible polymer-coated stent and to a process for the manufacturing thereof.

Stenosis resolution of cylindrically-shaped hollow biological structures, such as circulatory system vessels, esophagus, bile ducts, intestine, urinary tracts and respiratory tract, at present have several possibilities offered by surgery, endoscopy, radiology.

Sometimes the pathological entity does not allow surgical practice, in this case endoscopic operation or radiologic intervention are practised for palliative and/or curative purpose.

The use of stents, namely expandable devices which have the purpose to maintain the stenotic lumen patent, is a technique always in progress (K. C. Wright et al.; Radiology, 156:69–72, 1985; J. C. Palmaz et al.; ibid., 164:705–708, 1987; G. K. McLean et al., ibid., 170:961–967, 1989).

Present uses of stents refer to the treatment of stenosis of bile ducts, arterial vessels, esophagus, urinary tracts and respiratory tract. Stents are also used in repair of aneurysms.

The mesh structure of stents, while on one hand allows their percutaneous application through catheters and ensures the mechanical characteristics that maintain the lumen patency, on the other hand puts some problems according to specific cases. In the event of a stent implant in a blood vessels, stent structure may perturb haemodynamic, therefore increasing the risk of thrombus formation. If the stenosis is caused by neoplastic proliferation, ristenosis may occur after stent implant because of tumour cell infiltration through the meshes of the stent itself (Severini, Cozzi, Bellomi, Cigada, Tanzi; Biomateriali, ¾ (1990) 79–84).

In most cases, stents are made of metallic materials, particularly stainless steel, titanium, or shape-memory alloys (Ni—Ti alloys). Said materials meet the structural and mechanical requirements, but involve some problems of biocompatibility and allergy, particularly when they come in contact with blood.

EP 0 480 667, in the name of Cook Inc., discloses a self-expanding percutaneous stent (Gianturco stent) covered by a flexible sleeve which is open at both ends. The flexible sleeve is welded or pinched at the ends of the stent. In the same reference, the possibility to coat the stent with plastic material is mentioned, but no specific teaching about the material nor the coating technique is provided.

Song et al., Radiology, 1991.; 180:349–354, describe a Gianturco stent wrapped with a nylon mesh coated by silicon rubber, for the palliative treatment of esophagogastric neoplasm obstructions.

The stent obtained by Song et al. involves two kinds of still unsolved problems; the difficult retrieval of the introducer sheath, due to the friction between stent coating (silicon rubber) and the sheath itself, and the anchorage of the stent to the esophagus mucosa, where the stent may be moved from by mechanical stresses, due to peristalsis.

Alvarado, Palmaz, et al. (Radiology, 1989, 170:975–978) describe polymer-coated balloon expandable stents and their application in bile ducts. The polymers used therein are silicon rubber and polyethere urethane.

To date there is still the need to provide coated stents with improved mechanical and biocompatibility characteristics.

SUMMARY OF THE INVENTION

It has now been found that by coating a stent with a thermoplastic polycarbonate urethane, a prosthesis having excellent biomechanical characteristics for the treatment of stenosis and aneurysms is obtained. In particular, the inner surface of the polymer-coated stent is totally smooth, while the outer surface perfectly fits to the stent mesh structure. In this manner the so obtained stent presents the advantage of a smooth lumen surface, and therefore a better fluid hydrodynamic, together with a structure having improved biomechanical characteristics. At the same time, the polymer outer surface perfectly follows the development of the stent structure thus allowing an optimal interaction of the prosthesis with the lumen mucosa and the consequent non migration of the prosthesis itself from the implant site.

Several kind of biocompatible polymers are well-known, for example polyethyleneterephthalate, polytetrafluoroethylene (Teflon), polymethacrylates and various types of block copolymers belonging to the class of polyurethanes.

Polyether urethanes are known as suitable materials for implantable prosthesis, but have proved to be not very resistant to the attack by the biological environment where they are implanted (Pinchuck et al., 17th Annual Meeting of the Society for Biomaterials, 1991, Scottsdale, Ariz., USA).

Therefore, it is an object of the present invention to provide a polycarbonate urethane-coated stent and the coating process thereof.

The particular type of stent to be used in the present invention is not critical. Stents which are well-known to those skilled in the art can be used, both self-expandable, and balloon-expandable, such as Palmaz, Palmaz-Schatz, Gianturco, Gianturco-Roubin, Gianturco-Rosch, Strecker and memory-shape stents.

A preferred embodiment of the present invention provides the use of a coated Gianturco-Rosch stent and the variations thereof.

The biocompatible copolymer to be used according to the present invention is a polycarbonate urethane of the type disclosed in U.S. Pat. No. 5,133,742 (Pinchuck) and EP 0 461 375 (Corvita Corp.), i.e. one substantially completely devoid of ether linkages, and is marketed with the trade name Corethane®.

According to the present invention, stent coating must take in consideration the desired final characteristics of the prosthesis and its use.

The stent may be coated with a single copolymer layer or with more copolymer layers.

A further object of the present invention is a process for coating a stent, said process comprising the steps of:
a) positioning the stent in its expanded configuration on a horizontal rotating bearing;
b) rotating said bearing;
c) deposition of the copolymer on said stent while rotating; and
d) removing the coated stent from said rotating bearing.

In a typical embodiment of the present invention, the stent is put on a bearing made of a suitable material, Teflon for example, and then the bearing is rotated at a definite speed and a copolymer solution is deposed on the stent to be coated.

The copolymer is dissolved in a suitable organic solvent, such as dimethylacetamide, dimethylformamide, at a concentration ranging from 10 to 40%, preferably from 15 to 20%. Maximum bearing rotating speed is 20 rpm.

The following examples further illustrate the invention.

EXAMPLE 1

A segmented thermoplastic polycarbonate urethane (Corethane®) was used to coat a Gianturco-Rosch stent.

To this end, 10 g of Corethane® 80A, commercially available as a 44.84% solution, were added with 16.37 g of dimethylacetamide (DMAC), obtaining 26.37 g of a 17% Corethane® solution.

The solution was left in a thermostatic bath at 70°–75° C. under stirring for about 5–10 hours and subsequently to equilibrated ambient temperatures.

Two Gianturco-Rosch stents, one single-body stent having 8 mm diameter (stent A) and one double-body stent having 7 mm diameter (stent B) were used.

To carry out the coated stent, a horizontal shaft electric motor, rotating at the speed of 2 rpm, was used, wherein a teflon cylindric bearing having a diameter equal to the stent diameter, was mounted by means of a coupling gear. The stent was inserted on the cylindric bearing, the latter was fixed on the motor shaft and the rotation of the device was started.

The polymeric material solution was dropped by means of a pipette on the rotating metallic grid until a complete coating of the device was obtained.

The device was kept rotating in a fume hood for 24 hours until complete solvent evaporation took place. The stent was removed from the mandrel using distiled water as a detaching agent. A stent was coated with a copolymer monolayer of a thickness of about 0.1 mm.

EXAMPLE 2

According to the process described in Example 1, two Gianturco-Rosch stents, the same as the above ones, were coated using a polyether urethane known under the trade name Pellethane® 2363 80A by Dow Chemical.

EXAMPLE 3

In this Example the mechanical characteristics of the coated stent according to the invention (Example 1) were compared with stents coated with another kind of polyurethane.

External pressure stiffness tests

This test intends to evaluate the stent stiffness to an external pressure. The importance of such a test is that the stent in working conditions undergoes to an external pressure by the vessel or duct wall, which could decrease the lumen, thus lowering the device efficacy.

To carry out the tests, a device simulating the effect of a pressure exerted by a biological wall was carried out. Said device consists of two elements. The first is a rectangular plexiglas bearing (3×2.5 cm) wherein a slot (2×21 mm) was obtained. The second is an inextensible cloth ribbon. The ribbon is inserted in the plexiglas bearing forming an eyelet wherein the tested device is inserted.

By fixing the ribbon ends to the clamps of a microdynamometer it is possible to evaluate the strength necessary to determine a reduction of the stent diameter. The test was carried out both on coated stents and on the corresponding uncoated ones (stent C and D).

The results show that the coated stents have a higher stiffness to an external pressure than the uncoated stents, as shown in Table 1 below.

TABLE 1

| | Strength necessary to decrease diameter. | | | |
|---|---|---|---|---|
| DIAMETER DECREASE (mm) | STRENGTH (N) | | | |
| | Stent A | Stent C | Stent B | Stent D |
| 1 | 0.88 | 0.14 | 0.72 | 0.63 |
| 2 | 2.84 | 0.22 | 2.96 | 1.15 |
| 3 | 7.78 | 0.40 | 6.96 | 2.03 |
| 4 | 8.50 | 0.64 | 11.08 | 3.70 |

Adhesion test

Adhesion test intends to compare adhesion ability of the two polymer materials to the stent metallic structure (AISI 316 stainless steel). The choice of this test comes from the observation that better adhesion ability between polymeric material and metal tends to minimize the problems linked to the stent insertion in the catheter and its release in the biological environment. Accordingly, the results of said test are deemed to provide useful informations about better metal-polymer matching.

The test was carried out according to ASTM C 794-80.

Sample preparation

The above described polymer solution was poured into cylindrical molds sealed on a glass plate; 2 mm wide-metal stripes (AISI 316 stainless steel) were immersed in the molds.

The molds containing the solution and the steel stripes were put in a vacuum oven at 70° C. for 24 hours.

After complete solvent evaporation, samples, wherein part of the metal stripe was completely immersed in the polymeric material, sizing 5.4×20 mm, were thus obtained.

The instrument used for the tests was a microdynamometer (Minimat, Polymer Laboratories). Tests were carried out at a clamp separation speed of 3 mm/min until detachment of metal from polymer material.

The results are shown in Table 2 below.

TABLE 2

| Adhesion test of Corethane® and Pellethane® to stainless steel AISI 316. | | |
|---|---|---|
| | Corethane | Pellethane |
| Disjunction stress (MPa) | 0.43 | 0.34 |
| | 0.53 | 0.28 |
| | 0.50 | 0.26 |
| | 0.32 | 0.32 |
| | 0.54 | 0.40 |
| | 0.29 | 0.25 |
| | 0.31 | 0.31 |
| | 0.24 | 0.29 |
| Mean | 0.40 | 0.31 |
| Std. Dev. | 0.12 | 0.05 |

EXAMPLE 4

In this example the resistance of the coated stents according to the present invention to the biological environment, in the present case prolonged contact with bile, was assayed. Bile was withdrawn from patients suffering from extraepatic bile duct obstruction and contacted with coated stents according to the present invention.

After 1 month of contact, no bile deposits were observed on the polymer coating.

I claim:

1. In a prosthetic polymer coated stent selected from the group consisting of a Gianturco stent, a Gianturco-Roubin stent and a Gianturco-Rosch stent for implantation within an animal duct comprising an elongated metal mesh stent structure having a lumen, an inner lumen surface and an outer surface and a polymer coating extending completely over the elongated metal mesh stent structure, the improvement comprising:

the polymer coating being a thermoplastic polycarbonate urethane polymer coating and said coating having:

a smooth inner lumen surface to provide improved fluid hydrodynamics within the lumen; and an outer surface configured to the outer surface of the elongated metal mesh stent structure to promote interaction of the coated stent with and non-migration thereof within the animal duct.

2. A stent according to claim 1, wherein the polycarbonate urethane polymer is substantially completely devoid of ether linkages.

3. A stent according to claim 1, wherein a Gianturco-Rosch stent is a metal mesh stent structure.

4. A stent according to claim 1, wherein said stent is coated with a monolayer of said polymer.

5. A stent according to claim 1, wherein said metal mesh stent structure is coated with a multilayer of said polymer.

6. A stent according to claim 1, wherein said coated polymer is an evaporated solution coating.

7. A stent according to claim 6, wherein an organic solvent is used in said solution.

8. A stent according to claim 7, wherein dimethylacetamide is said solvent.

9. A stent according to claim 6, wherein the concentration of said polymer in the solution is between 10 to 40 w/w %.

10. A process for coating an elongated metal mesh expandable stent selected from the group consisting of a Gianturco stent, a Gianturco-Roubin stent and a Gianturco-Rosch stent for use as a prosthetic for implantation within an animal duct, said stent having a lumen, an inner lumen surface and an outer surface, comprising:

(A) positioning the stent in an expanded configuration on a horizontal rotatable support means;

(B) rotating the support means;

(C) depositing a polymer on said stent and support means while the support means and stent are being rotated, so as to coat the stent and support means, wherein a polymer coating extends completely over the elongated metal mesh stent, a smooth inner lumen surface of the polymer coating is provided to improve hydrodynamics within the lumen and an outer surface of the polymer coating is configured to the outer surface of the elongated metal mesh stent to promote interaction of the coated stent with and non-migration thereof within an animal duct; and (D) removing the so-coated stent from the support means.

11. The process of claim 10, wherein the stent is coated with a monolayer of the polymer.

12. The process of claim 10, wherein the stent is coated with a multilayer of the polymer.

13. The process of claim 10, wherein the support means has an outer surface of TEFLON.

14. The process of claim 10, wherein the support means is rotated at a speed of up to 20 rpm.

15. The process of claim 10, wherein the polymer is deposited on the stent and support means from a solution of the polymer and the solution is evaporated to produce the coating.

16. The process of claim 15, wherein the solution has an organic solvent.

17. The process of claim 16, wherein the organic solvent is dimethylacetamide.

18. The process of claim 15, wherein the concentration of the polymer in the solution is between 10 and 40 w/w%.

* * * * *